(12) United States Patent
Boozari

(10) Patent No.: US 10,232,084 B1
(45) Date of Patent: Mar. 19, 2019

(54) METHOD FOR RETAINING DEMINERALIZED BONE MATRIX PARTICLES

(71) Applicant: NuVasive, Inc., San Diego, CA (US)

(72) Inventor: Habib Boozari, Hacienda Heights, CA (US)

(73) Assignee: NuVasive, Inc., San Diego, CA (US)

(*) Notice: Subject to any disclaimer, the term of this patent is extended or adjusted under 35 U.S.C. 154(b) by 184 days.

(21) Appl. No.: 14/735,128

(22) Filed: Jun. 9, 2015

Related U.S. Application Data

(63) Continuation of application No. 13/457,478, filed on Apr. 26, 2012, now abandoned.

(60) Provisional application No. 61/479,378, filed on Apr. 26, 2011.

(51) Int. Cl.
*A61L 27/36* (2006.01)
*B01D 37/00* (2006.01)

(52) U.S. Cl.
CPC .......... *A61L 27/3691* (2013.01); *B01D 37/00* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 2,384,057 | A * | 9/1945 | Wetherell | B01D 35/02 210/445 |
| 7,758,556 | B2 * | 7/2010 | Perez-Cruet | A61F 2/4644 604/317 |
| 2012/0109227 | A1 * | 5/2012 | Farley | A61F 2/4644 606/86 R |

\* cited by examiner

*Primary Examiner* — Benjamin M Kurtz
(74) *Attorney, Agent, or Firm* — NuVasive, Inc.

(57) ABSTRACT

A method for retaining demineralized bone matrix particles within a container utilizing a filter device is provided. The method is performed during surgical procedures where bone graft containing demineralized bone matrix particles is used. The filter device is dimensioned for use with a container having a mixture of bone graft material including demineralized bone matrix particles and liquid, whereby the filter device is placed in the container, the liquid is poured off through the pores in the filter device, and the demineralized bone matrix particles are retained with bone graft material in the container.

14 Claims, 9 Drawing Sheets

METHOD FOR RETAINING DEMINERALIZED BONE MATRIX PARTICLES

CROSS REFERENCE TO RELATED APPLICATION

This application is a continuation of U.S. patent application Ser. No. 13/457,478, field Apr. 26, 2012, which claims the benefit of the filing date of U.S. Provisional Application No. 61/479,378 which was filed on Apr. 26, 2011. The entire contents of U.S. Provisional Application No. 61/479,378 is incorporated herein by reference.

TECHNICAL FIELD

This document relates to filter devices, and more specifically to a filter device which is dimensioned for use with a container for separating bone graft material from liquid mixture.

BACKGROUND

Bone grafting is a surgical procedure by which a new bone or a replacement material is placed into spaces between or around broken bone to aid in healing. Demineralised Bone Matrix (DBM) is often a component of a bone graft substitute which acts as an osteoconductive as well as osteoinductive material which is capable to improve the rate of new bone formation and to potentially reduce the risk and pain associated with the procedure.

SUMMARY OF THE EMBODIMENT

According to an embodiment, the filter comprises frame with an interrupted perimeter and a screen attached to the frame. By way of example, the filter device comprises a split ring component and having top surface and a bottom surface and a screen having a plurality of pores attached to one of the top and bottom surfaces. The filter device is configured to be inserted into and fit within the inner perimeter of a container. The container is configured to hold a mixture of bone graft material and liquid. The bone graft material includes Demineralised Bone Matrix (DBM) particles. The liquid in the mixture may be at least one of a cryoprotectant, water, saline solution or any other suitable wash solution. The frame is dimensioned to complement the interior of the container. The filter can be pushed down to the interior of the container until it rests against DBM containing bone graft material. After that, the liquid mixture can be poured off through the pores in the filter device while the DBM containing the bone graft material remains in the container. The pores are sized smaller than DBM particles to prevent the DBM particles from separated from the bone graft material with the liquid. For instance pores may range in size from 50 micrometer to 150 micrometer. Optionally, the filter may be subsequently pulled up in and/or removed from the container and more liquid can be added to the bone graft material, then the filter can be pushed down and the liquid can be poured off again. Due to the presence of interrupted perimeter of the split ring the filter device is adaptable to changes in the circumference of the container as the position of the filter device is changed within the container. The filter device can be inserted into the interior circumference of the container and closed with a lid. The presence of the lid allows the DBM particles containing bone graft material to be securely placed inside the container during transportation.

Another embodiment of a filter device is designed in the form of a hollow container. The filter device comprises of a plurality of pores. The filter device is dimensioned to fit within a container, wherein the filter device and the interior of the container possess corresponding shapes. The container is configured to hold a mixture of bone graft material and the liquid. The filter device is hollow to allow the bone graft material and the liquid mixture to be placed inside the filter device, which is placed inside the container. When the filter device is removed from the container, the liquid will flow out of the plurality of pores and separate from the DBM-containing bone graft material which remains in the hollow interior of the filter device.

An alternative embodiment of a filter device is designed in the form of a lid for a container. The lid is dimensioned to be placed over the open end of a container. The filter device comprises of a screen having a plurality of pores. The container is configured to hold a mixture of DBM-containing bone graft material and liquid. The plurality of pores are sized smaller than DBM particles to prevent DBM particles from being separated from the bone graft material with the liquid. The filter device also includes a vent for improving the flow of fluid into and out of the container when the filter device is in use. The liquid can be poured out of the container through the screen portion of the lid and the DBM-containing bone graft material is retained within the container. The liquid in the container may be at least one of a cryoprotectant, water, saline solution or any other suitable wash solution.

Another alternative embodiment of a filter device is designed in the form of a lid for a container. According to this embodiment, the lid is dimensioned to be placed over the open end of the container. The filter device comprises of a plurality of pores. The plurality of pores allows the liquid to be separated from the DBM-containing bone graft material by pouring the liquid out of the container while the filter device is held over the open end of the container.

Yet another embodiment of a filter device is designed in the form of a lid for a container. The lid is dimensioned to be placed over the open end of a container. The filter device comprises a screen made of mesh fabric with a plurality of pores. The container is configured to hold a mixture of bone graft material and liquid. The liquid can be poured out of the container through the screen of the lid while the DBM containing bone graft material is retained within the container.

Yet another alternative embodiment of a filter device is designed in the form of a mesh bag. The filter device is comprised wholly of mesh fabric having a plurality of pores. The filter device is dimensioned to fit inside a container. The filter device is hollow to allow the bone graft material and the liquid mixture to be placed inside the filter device, which is placed inside the container. When the filter device is removed from the container, the liquid mixture will flow out of the plurality of pores and thus get separated from the DBM containing bone graft material which remains in the hollow interior of the filter device. The plurality of holes is sized smaller than DBM particles to prevent DBM particles from being separated from the bone graft material with the liquid mixture.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION

Illustrative embodiments of the filter device are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

The present description illustrates a filter device dimensioned to fit within a container of bone graft material and liquid mixture, wherein the bone graft material includes demineralized bone matrix (DBM). The filter device is configured to retain bone graft material and DBM and prevents the loss of DBM particles from the bone graft when the liquid is separated from the mixture.

Figures 1A, 1B:
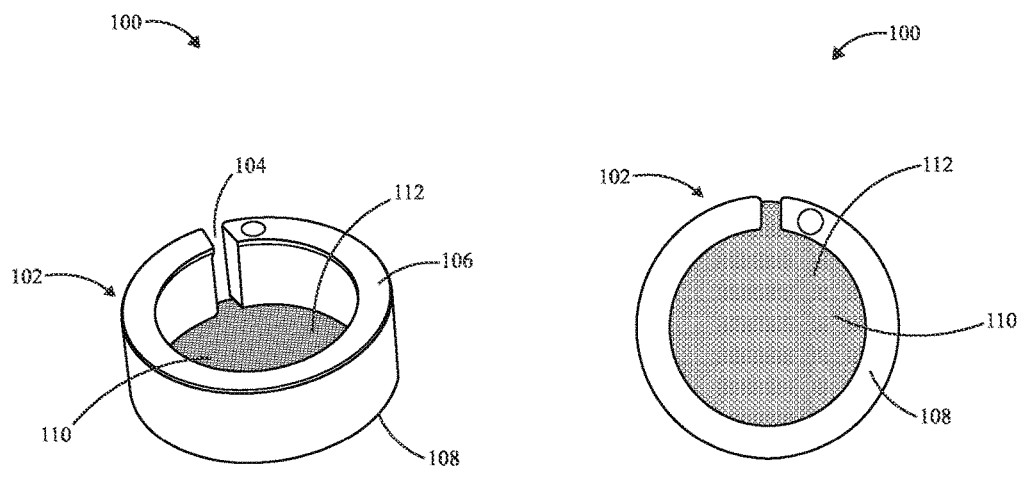
FIG. 1A is a perspective view of a filter device according to an exemplary embodiment.
FIG. 1B is a bottom top view of the filter device according to an exemplary embodiment.
Figures 1C, 1D:
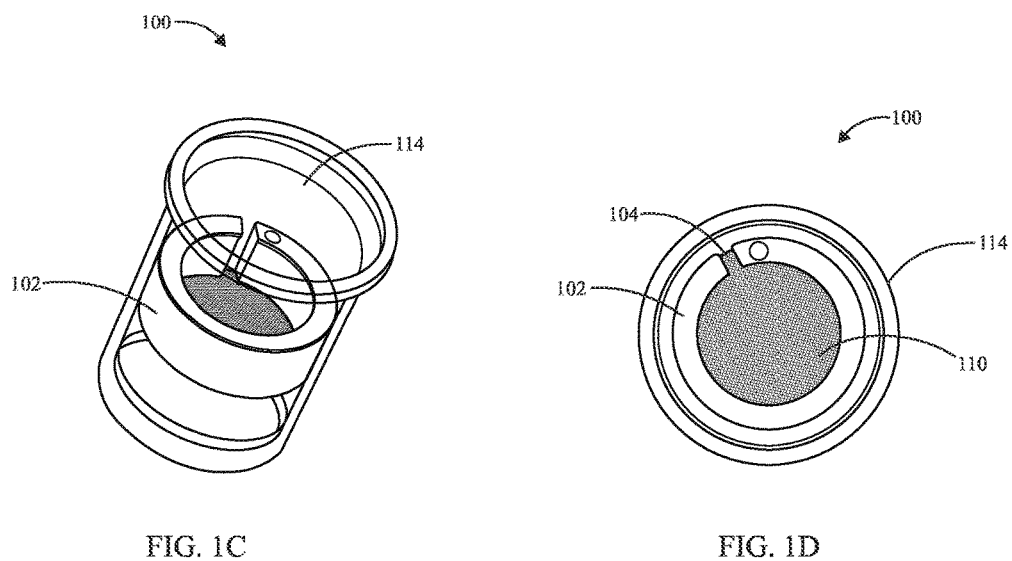
FIG. 1C is a perspective view of the filter device according to an exemplary embodiment inserted into an interior of a container.
FIG. 1D is a top view of the filter device according to an exemplary embodiment inserted into the interior of the container.
Figures 1E, 2A:
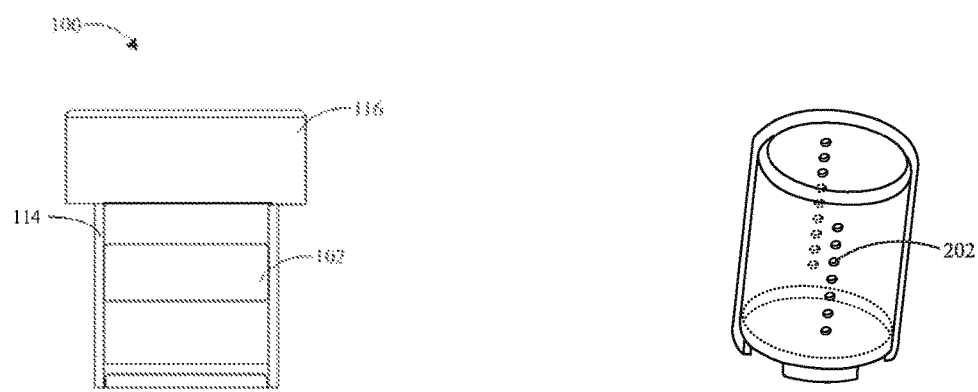
FIG. 1E shows the filter device inserted into the interior of the container and closed with a lid.
FIG. 2A is a perspective view of another embodiment of a filter device.

Referring now to FIGS. 1A through 1E, an embodiment of a filter device 100 is illustrated. The filter device includes a frame 102 with an interrupted perimeter and having a top surface 106 and a bottom surface 108 and a screen 110 attached to the frame 102. As shown in FIGS. 1A and 1B, an exemplary embodiment of the filter device 100 comprises a frame in the form of a split ring 102. A screen 110 having a plurality of pores 112 is attached to the frame 102 on the bottom surface 108. It will be appreciated that the screen could alternatively be attached to the top surface 106 of the frame 102. FIGS. 1C and 1D show the exemplary embodiment of the filter device 100 inserted into an interior of a container 114. The container 114 is configured to hold a mixture of bone graft material and liquid (not shown). The bone graft material includes DBM particles. The liquid in the container 114 may be at least one of a cryoprotectant, water, saline solution or any other suitable bone graft storage or wash solution. The frame 102 is dimensioned to complement the interior of the container 114. The filter 100 can be pushed down to the interior of the container 114 until it rests against DBM containing bone graft material. Thereafter, the liquid mixture can be poured off through the pores 112 in the screen 110 and DBM containing the bone graft material remains in the container 114. The pores 112 are sized smaller than DBM particles to prevent the DBM particles from separated from the bone graft material with the liquid mixture. For instance, pores 112 may have varied sizes in a range from 50 micrometer-150 micrometer. Optionally, the filter 100 may be subsequently pulled up in or removed from the container 114 and more liquid can be added to the bone graft material, then the filter 100 can be pushed down and the liquid can be poured off again. Due to the presence of interrupted perimeter 104 of the split ring 102, the filter device 100 is adaptable to changes in the circumference of the container 114 as the position of the filter device 100 is changed within the container 114. The position of the filter device 100 is changed within the container 114 due to the presence of any biocompatible material capable of plastically deforming to accommodate the circumference of the container 114. FIG. 1E shows the filter device 102 inserted into the interior circumference of the container 114 and closed with a lid 116. The presence of the lid 116 allows the Demineralised Bone Matrix (DBM) particles containing bone graft material to be securely placed inside the container 114 during transportation.

Figure 2B:
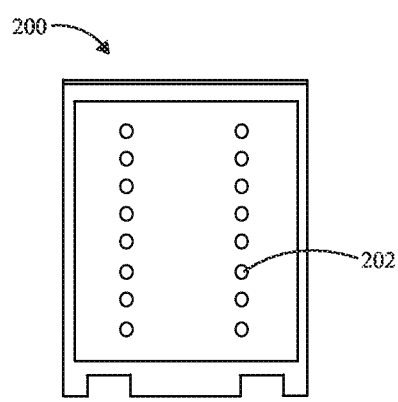
FIG. 2B is a front view of another embodiment of the filter device.

Referring to FIGS. 2A-2B, another embodiment of a filter device 200 is designed in the form of a hollow container having a plurality of pores. The filter device 200 is dimensioned to fit within a container, wherein the filter device 200 and the container possess corresponding shapes. The filter device 200 is hollow to allow the bone graft material and the liquid mixture to be placed inside the filter device 200, which is placed inside the container. When the filter device 200 is removed from the container, the liquid mixture will flow out of the plurality of pores 202 and thus separate from the DBM containing bone graft material which remains in the hollow interior of the filter device 200. The plurality of pores 202 are sized smaller than DBM particles to prevent DBM particles from being separated from the bone graft material with the liquid mixture. It will be appreciated that while shown in FIGS. 2A-2B as cylindrical, the filter device can be any shape corresponding to the shape of the interior of the container with which it is used.

Figures 3A, 3B, 3C:
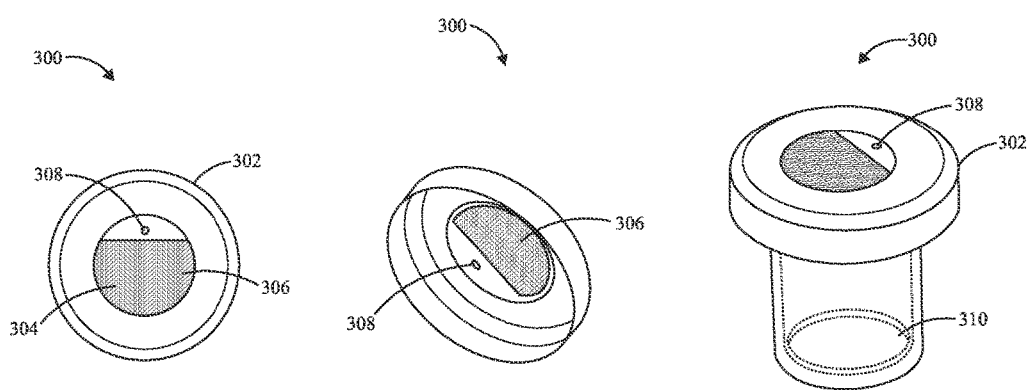
FIG. 3A is a top view of an alternative embodiment of a filter device.
FIG. 3B is a bottom perspective view of the alternative embodiment of the filter device.
FIG. 3C is a perspective view of an alternative embodiment of the filter device in which the filter device.

As shown in FIGS. 3A to 3C, an alternative embodiment of a filter device 300 is designed in the form of a lid for a container. The filter device 300 in this embodiment is similar to that of the embodiment described in FIG. 1A, except that the filter device 300 is designed in the form of a lid 302 for a container and also includes a vent 308 for improving the flow of fluid into and out of the container. Accordingly, the filter device 300 in this embodiment comprises of a screen 304 having a plurality of pores 306. The lid 302 is dimensioned to be placed over the open end of a container 310. The container 310 is configured to contain a mixture of bone graft material containing DBM and liquid (not shown). The plurality of pores 306 are sized smaller than DBM particles to prevent DBM particles from being separated from the bone graft material when the liquid is removed from the mixture. The filter device 300 also includes a vent 308 for improving the flow of fluid into and out of the container 310 when the filter device 300 is in use. The filter device 300 can be placed over the open end of the container 310. The liquid mixture can be poured out of the container 310 through the screen portion 304 of the lid 302 and the DBM containing bone graft material is retained within the container 310.

Figures 4A, 4B:
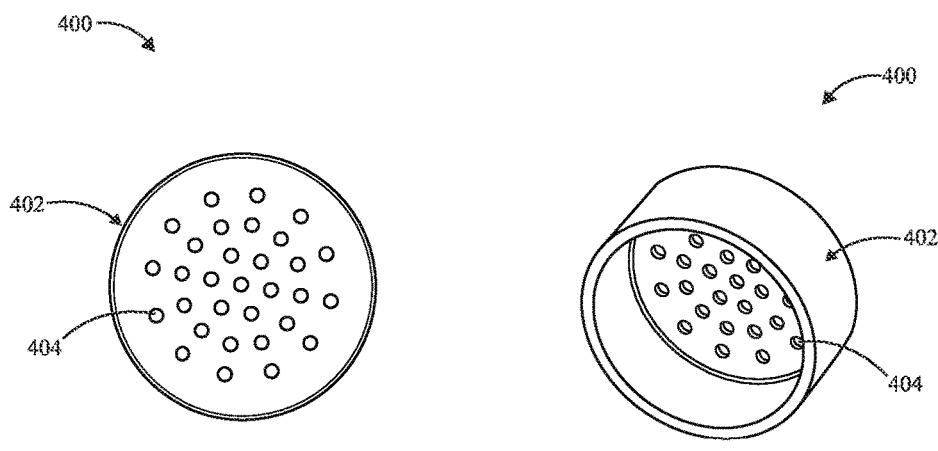
FIG. 4A is a front view of another alternative embodiment of a filter device.
FIG. 4B is a perspective view of another alternative embodiment of the filter device.

FIGS. 4A and 4B show another alternative embodiment of a filter device 400 designed in the form of a lid for a container. According to this embodiment, the lid 402 is dimensioned to be placed over the open end of the container as shown in FIG. 3C. The container as shown in FIG. 3C is configured to hold a mixture of DBM-containing bone graft material and liquid. The filter device 400 comprises of a plurality of holes 404. The plurality of holes 404 are sized smaller than DBM particles to prevent DBM particles from being separated from the bone graft material when the liquid is removed. The plurality of holes 404 allow the liquid component to be separated from the DBM containing bone graft material by pouring the liquid out of the container while the filter device 400 is held over the open end of the container as shown in FIG. 3C.

Figures 5A, 5B:
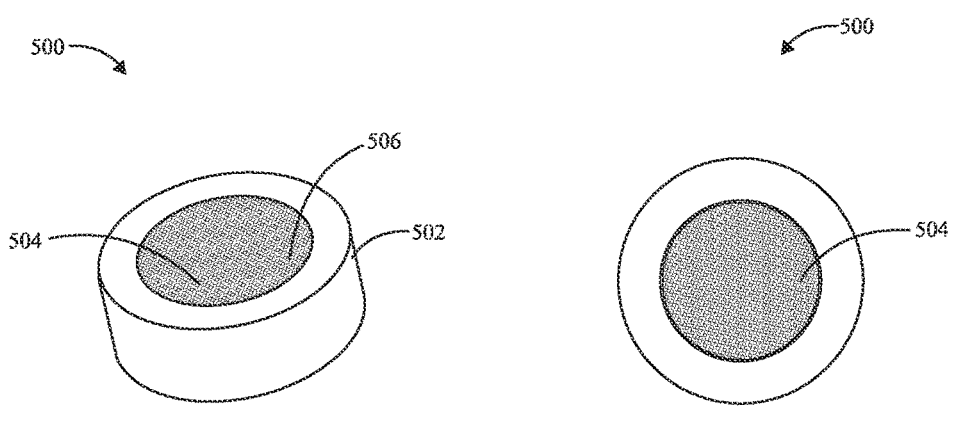
FIG. 5A is a perspective view of yet another embodiment of a filter device.
FIG. 5B is a bottom view of yet another embodiment of the filter device.

Referring to FIGS. 5A and 5B, yet another embodiment of a filter device 500 is designed in the form of a lid for a container. The filter device 500 in this embodiment is similar to that of the embodiment described in FIG. 1A, except that the filter device 500 comprises a screen with a plurality of pores. The filter device 500 comprises a screen 504 made of mesh fabric with plurality of pores 506. The lid 502 is dimensioned to be placed over the open end of a container, such as the one shown in FIG. 3C. The container as shown in FIG. 3C is configured to contain a mixture of DBM-containing bone graft material and liquid. The plurality of pores 506 are sized smaller than DBM particles to prevent DBM particles from being separated from the bone graft material with the liquid. The filter device 500 can be placed over the open end of the container as shown in FIG. 3C. The liquid mixture can be poured out of the container through the screen portion 504 of the lid 502.

Figure 6:
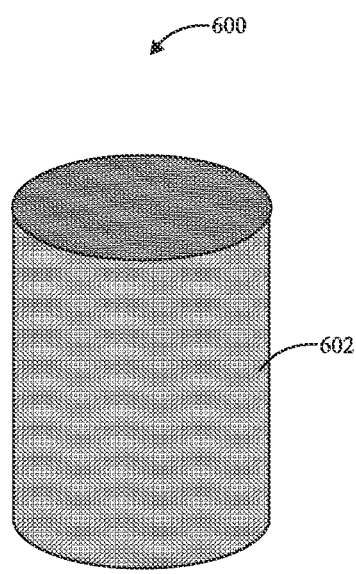
FIG. 6 is a perspective view of yet another alternative embodiment of a filter device.

FIG. 6 shows yet another alternative embodiment of a filter device 600 designed in the form of a mesh bag. The filter device 600 is made wholly of mesh fabric having a plurality of pores 602. The filter device 600 is dimensioned to fit in a container. The container is configured to hold a mixture of DBM-containing bone graft material and liquid. The filter device 600 is hollow to allow the bone graft material and the liquid mixture to be placed inside the filter device, which is placed inside the container. When the filter device 600 is removed from the container the liquid will flow out of the plurality of holes and separate from the DBM-containing bone graft material which remains in the hollow interior of the filter device 600. The plurality of holes 602 are sized smaller than DBM particles to prevent DBM particles from being separated from the bone graft material with the liquid.

Figure 7:
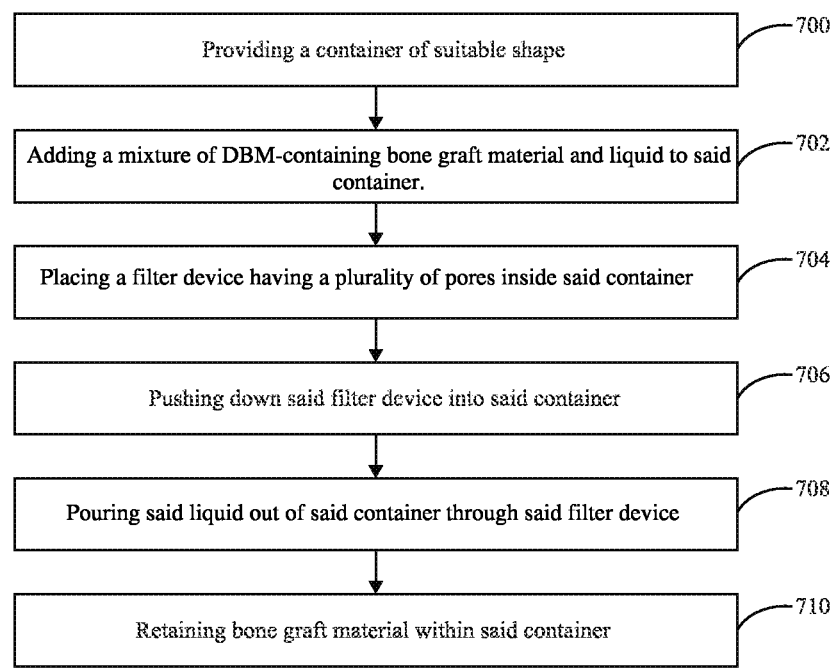
FIG. 7 shows a flowchart illustrating a method for retaining bone graft material within a container utilizing the filter device.

FIG. 7 shows a flowchart illustrating a method for retaining the DBM component of bone graft material within the bone graft material when separating the bone graft material from a liquid utilizing the filter device as shown in FIGS. 1A-1E. The method is initiated by providing a container of suitable shape as shown in block 700. Then a mixture of liquid and DBM-containing bone graft material is added to the container as indicated at block 702. A filter device having a plurality of pores is then placed inside said container as shown in block 704. Thereafter, the filter device is pushed down into said container as shown in block 706. Then the liquid is poured out of the container through the filter device as indicated at block 708. Upon separating the liquid from the bone graft material, the bone graft material, including the DBM component, is retained within the container 710.

According to alternative embodiments, the above described method may further include a wash step, wherein after the liquid is initially separated from the bone graft material, another liquid is added to the bone graft material and then poured off again through the filter. This wash step may be repeated as desired by the user. According to another embodiment, the method may compromise the steps of (1) providing a container, (2) adding a mixture of DBM-containing bone graft material and liquid to the container, (3) placing a filter device having a plurality of pores in the form of a lid over an open end of the container, (4) pouring the liquid out of the container through the filter device, and (5) retaining the bone graft material, including the DBM component, inside the container. This alternative embodiment may also further include a wash step as described above.

According to yet another embodiment, the method may comprise the steps of (1) providing a container, (2) placing a hollow filter device having a plurality of pores inside said container, (3) adding a mixture of DBM-containing bone graft material and liquid to said container inside of said hollow filter device, (4) removing said hollow filter device from said container, (5) allowing liquid to separate from the bone graft material through the plurality of holes in the hollow filter device, and (6) retaining said bone graft material, including the DBM component, within said hollow filter device. This embodiment may optionally include a further steps of replacing the hollow filter device including the bone graft material in the container, adding another liquid to the bone graft material and then allowing the liquid to separate from the bone graft material by removing the hollow filter device from the container and allowing the liquid to flow through the plurality of pores in the filter device.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention.

What is claimed is:

1. A method for separating liquid and retaining bone graft material from a mixture of DBM-containing bone graft material and liquid held within a container, said method comprising the steps of:

advancing a filter device from a first elevated position within the container to a second position wherein the filter device rests against the DBM-containing bone graft material, the filter device including a screen and compressible split-ring frame having an upper surface, a lower surface, and an open gap extending through the upper and lower surfaces, the screen including a plurality of pores dimensioned to inhibit passage of DBM particles while passing liquid therethrough; and pouring the liquid out of the container while the DBM-containing bone graft material is retained within the container beneath the filter device.

2. The method of claim 1, further comprising adding additional liquid to the DBM-containing bone graft material retained within the container after the step of pouring out the liquid.

3. The method of claim 2, further comprising pouring out the additional liquid while the DBM-containing bone graft material is retained within the container beneath the filter device.

4. The method of claim 1, wherein the plurality of pores have pore sizes ranging from 50 micrometers to 150 micrometers.

5. The method of claim 1, wherein the screen is attached to the bottom surface of the compressible split-ring frame, and the screen extends in a plane parallel to the lower surface of the compressible split-ring frame.

6. The method of claim 1, wherein the liquid is at least one of a cryoprotectant, water, and saline solution.

7. The method of claim 1, wherein the compressible split-ring frame comprises a first end and a second end on either side of the open gap extending between the upper and lower surfaces, and wherein the first end and second end do not overlap each other when viewed from above the upper surface of the compressible split-ring frame, wherein the compressible split-ring frame lower surface defines a lower plane passing therethrough, and wherein the screen extends in planar form in alignment with the lower plane.

8. A method for removing liquid from a mixture of DBM-containing bone graft material and liquid held within a container, wherein the container is provided with the DBM-containing bone graft material mixed with a first liquid which is a cryoprotectant liquid, the method comprising:

advancing a filter device from a raised position within the container to a lowered position, wherein in the lowered position the filter device rests against the DBM-containing bone graft material, the filter device including a screen and compressible split-ring frame having an upper surface, a lower surface, and an open gap extending through the upper and lower surfaces, the screen including a plurality of pores dimensioned to inhibit passage of DBM particles while passing the cryoprotectant liquid therethrough; and pouring the cryoprotectant liquid out of the container while the DBM-containing bone graft material is retained within the container beneath the filter device.

9. The method of claim 8, further comprising, after pouring the cryoprotectant liquid out of the container:

pulling up the filter device;

adding a second liquid to the DBM-containing bone graft material retained within the container.

10. The method of claim 9, further comprising, after adding the second liquid to the DBM-containing bone graft material:

pushing the filter device down against the DBM-containing bone graft material.

11. The method of claim 9, further comprising, after adding the second liquid to the DBM-containing bone graft material:

pouring out the second liquid while the DBM-containing bone graft material is retained within the container beneath the filter device.

12. The method of claim 11, wherein the second liquid is a washing liquid.

13. The method of claim 8, wherein the compressible split-ring frame is configured to radially engage an interior circumference of the container and to slide up and down within the container responsive to being pulled up or pushed down.

14. The method of claim 13, wherein the screen extends in a plane extending across the lower surface of the compressible split-ring frame.

* * * * *